(12) United States Patent
Reynolds et al.

(10) Patent No.: US 9,072,856 B2
(45) Date of Patent: Jul. 7, 2015

(54) CPAP STABILIZING HAT

(76) Inventors: Paula Reynolds, Glenville, NY (US);
Lori Anne Metzgar, BurntHills, NY (US)

(*) Notice: Subject to any disclaimer, the term of this patent is extended or adjusted under 35 U.S.C. 154(b) by 574 days.

(21) Appl. No.: 13/204,782

(22) Filed: Aug. 8, 2011

(65) Prior Publication Data

US 2013/0037022 A1    Feb. 14, 2013

(51) Int. Cl.
| | |
|---|---|
| A62B 18/08 | (2006.01) |
| A62B 9/00 | (2006.01) |
| A62B 18/02 | (2006.01) |
| A61F 9/00 | (2006.01) |
| A42B 1/04 | (2006.01) |
| A42C 5/04 | (2006.01) |
| A61M 16/06 | (2006.01) |

(52) U.S. Cl.
CPC ....... *A61M 16/0683* (2013.01); *A61M 16/0666* (2013.01)

(58) Field of Classification Search
None
See application file for complete search history.

(56) References Cited

U.S. PATENT DOCUMENTS

| | | | | |
|---|---|---|---|---|
| 2,292,568 A * | 8/1942 | Kanter et al. | ............ | 128/203.28 |
| 2,376,871 A * | 5/1945 | Fink | .......... | 128/201.19 |
| 3,068,865 A * | 12/1962 | Laszlo | ..... | 128/200.28 |
| 4,018,221 A * | 4/1977 | Rennie | ..... | 128/207.18 |
| 4,319,136 A * | 3/1982 | Jinkins | ....... | 378/4 |
| 4,738,119 A * | 4/1988 | Zafred | ............ | 607/104 |
| 4,739,757 A * | 4/1988 | Edwards | .......... | 128/207.18 |
| 4,774,946 A * | 10/1988 | Ackerman et al. | ....... | 128/207.18 |
| 5,188,101 A * | 2/1993 | Tumolo | ..... | 128/207.18 |
| 5,517,986 A * | 5/1996 | Starr et al. | ....... | 128/206.24 |
| 5,940,880 A * | 8/1999 | Phillips | ............... | 2/7 |
| 6,156,059 A * | 12/2000 | Olofsson | ......... | 607/109 |
| 6,241,575 B1 * | 6/2001 | Shailer | ............. | 450/38 |
| 6,889,689 B1 * | 5/2005 | Neuman | ......... | 128/201.22 |
| 7,779,832 B1 | 8/2010 | Ho | | |
| 7,913,692 B2 | 3/2011 | Kwok | | |
| 7,931,023 B2 | 4/2011 | Berthon-Jones et al. | | |
| 7,938,116 B2 | 5/2011 | Ging et al. | | |
| 7,942,148 B2 | 5/2011 | Davidson et al. | | |
| 2003/0034030 A1 * | 2/2003 | Carlucci et al. | ....... | 128/200.24 |
| 2004/0025884 A1 * | 2/2004 | McKown | ......... | 128/207.18 |
| 2005/0061326 A1 * | 3/2005 | Payne, Jr. | ........ | 128/206.11 |
| 2006/0179544 A1 * | 8/2006 | Knievel | ....... | 2/181 |
| 2007/0214544 A1 * | 9/2007 | Mitchell | ......... | 2/171 |
| 2008/0190435 A1 * | 8/2008 | Hansen | ......... | 128/207.18 |
| 2010/0031428 A1 * | 2/2010 | Paull | ............... | 2/458 |
| 2010/0275343 A1 * | 11/2010 | Gibson et al. | ........... | 2/209.13 |

OTHER PUBLICATIONS

Instruction sheet, "CookieCap CPAP Stabilizing Cap," Hawaii Medical, LLC, 2008.
Instruction sheet, "Infant Nasal CPAP Cannula", © 2007 Teleflex Incorporated, 81690-13 May 2007.

* cited by examiner

*Primary Examiner* — Tan-Uyen (Jackie) T Ho
*Assistant Examiner* — Eric Bryant
(74) *Attorney, Agent, or Firm* — Cesari and McKenna, LLP; William J. Mostyn

(57) ABSTRACT

Ventilation apparatus includes a hat having an axis of symmetry and composed of a top and sides extending down to a rim extending all around the hat. An elongated flexible panel encircles the rim. Securements secure the panel to the rim at spaced-apart locations therearound to provide a plurality of relatively long channels extending between the rim and the panel. Each channel extends parallel to the axis and is sized to slidably receive a tube. In use, a patient wears the hat and inlet and outlet tubes are retained in selected hat channels so as to stabilize a patient interface cannula connected to the tubes so that the cannula's nasal prongs remain properly positioned in the patient's nares.

20 Claims, 3 Drawing Sheets

CPAP STABILIZING HAT

BACKGROUND OF THE INVENTION

This invention relates to continuous positive airway pressure (CPAP) ventilation apparatus. It relates more particularly to a hat for stabilizing a CPAP patient interface used to provide oxygen to neonates and infants.

Many sick and premature infants require the aid of CPAP ventilation to deliver oxygen to them. In fact, such ventilation is used in practically all neonatal care units of hospitals. A typical CPAP ventilator interface includes a dual prong nasal cannula with inspiratory and expiratory elbows at opposite ends thereof. The nasal cannula may be connected to a ventilator circuit comprising a long flexible inlet tube leading from a source of oxygen under pressure to the inspiratory elbow of the cannula and a similar long outlet tube extending from the expiratory elbow of the cannula to an isolated exhaust line. Typically, these connecting tubes may be as long as five or six feet in order to reach an infant lying in a hospital crib. In use, the flexible prongs of the nasal cannula are inserted into a patient's nares and the aforesaid tubes are secured to the patient's head in some way in an attempt to stabilize the cannula so that the prongs thereof remain in place without exerting undo pressure on the walls of the patient's nasal passages and septum.

Various devices have been used in the past to help stabilize the CPAP nasal cannula. However, all have drawbacks which militate against their wider use and application. One prior device of which we are aware is quite complicated in requiring the use of at least three separate straps which must be secured by Velcro® fasteners around the infant's head and chin and wrapped around the tubing. In accordance with other prior techniques, Velcro® tape is wrapped around the tubing and mated to separate Velcro® strips adhered to a hat worn by the infant or the tubing tapes are secured by elastics pinned to that hat. In the former case, the mating Velcro® strips may become separated or the adhesive strips may pull away from the hat. In the latter case, the pins may be pressed against the infant's skin causing discomfort or they may open accidentally presenting a safety hazard. Also, the elastics allow excessive side-to-side movement of the tubes.

In any event, none of the prior stabilizing devices and techniques sufficiently restrains the CPAP nasal cannula given the long inlet and outlet tubes attached thereto. These tubes exert considerable destabilizing forces on the cannula when the infant is repositioned in his/her crib or is removed therefrom in order to be held and comforted by parents. Resultantly, the prongs of the nasal cannula may be pulled out of the infant's nose thereby depriving the infant of oxygen or the prongs may cause distortion of the nasal walls resulting in patient discomfort.

SUMMARY OF THE INVENTION

Accordingly, this invention aims to provide improved apparatus for stabilizing a CPAP patient interface.

Another object of the invention is to provide such apparatus which is particularly suitable for neonates and infants.

A further object of the invention is to provide apparatus of this type which is simple and very easy to use.

An additional object of the invention is provide such stabilizing apparatus which can be accommodated to infants having a wide variety of head sizes.

Still another object is to provide stabilizing apparatus which has an improved aesthetic appearance as compared to prior devices of this type.

Yet another object of the invention is to provide a stabilizing hat for securing the tubes extending to and from a patient interface that supplies oxygen to an infant.

Yet another object of the invention is to provide a hat of this type which is relatively easy and inexpensive to manufacture.

Other objects will, in part, be obvious and will, in part, appear hereinafter.

The invention accordingly comprises the features of construction, combination of elements and arrangement of parts which will be exemplified in the construction hereinafter set forth, and the scope of the invention will be indicated in the claims.

Briefly, the present CPAP ventilation apparatus comprises a hat of flexible material having an axis of symmetry. The hat is composed of a crown and sides which extend down to a rim extending all around the hat. An elongated flexible panel encircles the rim and is secured thereto at spaced-apart locations therearound to provide a plurality of relatively long channels between the rim and the panel which channels extend parallel to said axis and are sized to slidably receive ventilator tubing.

In a preferred embodiment of the invention, the sides of the hat are folded up to form a two-ply rim and the panel is composed of a plurality of layers which are secured to the rim by lines of stitching which extend through all of the panel and rim layers so that the channel walls are stiffened by a plurality of plies.

In use, the stabilizing hat may be placed on an infant's head and the ventilation tubing serving the interface cannula that provides oxygen to the infant may be threaded through one or another of the channels in the hat before being connected in the ventilation circuit. After the cannula's nasal prongs are inserted into the patient's nares, the tubes may be adjusted along their respective channels until the cannula is properly positioned on the patient, i.e., so as to extend more or less perpendicular to the axis of the hat. Thereafter, the walls of the channels resiliently engage the tubes to inhibit further movement thereof relative to the hat. Resultantly, the tubes are held in position more or less parallel to the axis of the hat thereby stabilizing the interface even though the infant moves around in the crib or is repositioned by a nurse as must be done on a regular basis.

BRIEF DESCRIPTION OF THE DRAWINGS

For a fuller understanding of the nature and objects of the invention, reference should be made to the following detailed description taken in connection with the accompanying drawings, in which.

DETAILED DESCRIPTION OF AN ILLUSTRATIVE EMBODIMENT

Figure 1:
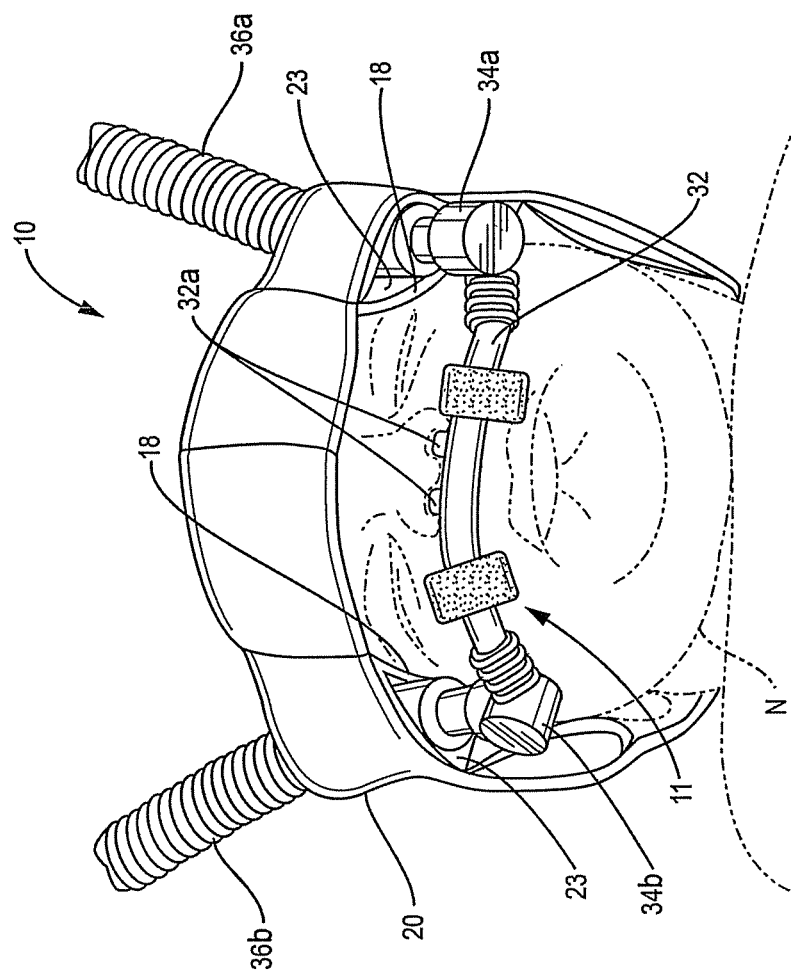
FIG. 1 is a perspective view of a reclining neonate receiving oxygen from CPAP ventilation apparatus stabilized according to the invention.

Referring to FIG. 1 of the drawings, a stabilizing hat 10 according to the invention is shown being worn by a reclining neonate N in order to stabilize a ventilator patient interface indicated generally at 11 that delivers oxygen to the neonate. Preferably, the hat is of a soft, flexible knitted or woven material.

Figure 2:
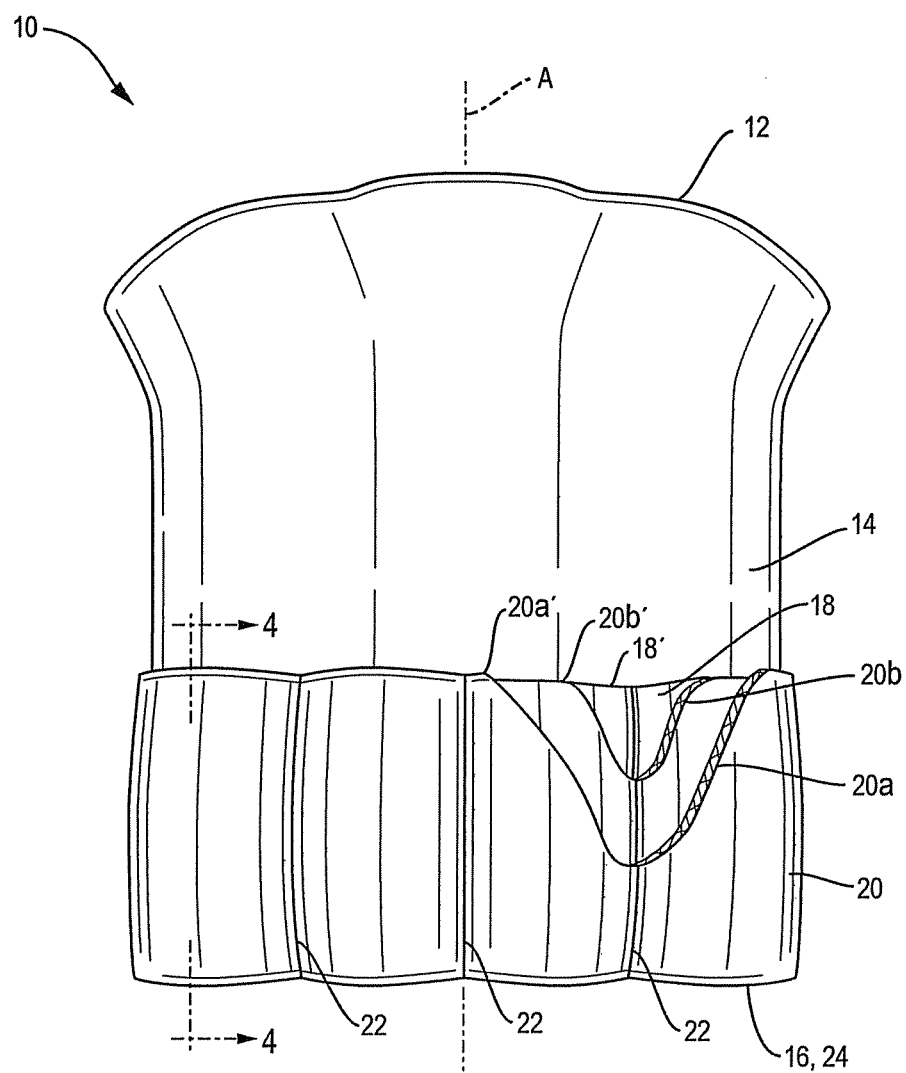
FIG. 2 is a side elevational view of the stabilization hat component of the FIG. 1 apparatus.

As shown in FIG. 2, hat 10, which has a vertical axis of symmetry A, comprises a top or crown 12 and side walls 14 which extend down to a fold line 16 at the bottom of the hat. At line 16, those walls are folded back on themselves to form an outer ply or band 18 which extends all around the hat. That ply 18 has an upper edge 18'. Thus, ply 18 and the underlying lower portion of the sidewalls 14 comprise a two-ply rim 19 best seen in FIGS. 3 and 4. Of course, if the ply or band 18 is not present, the rim 19 is constituted solely by the lower portions of side walls 14.

Figure 4:
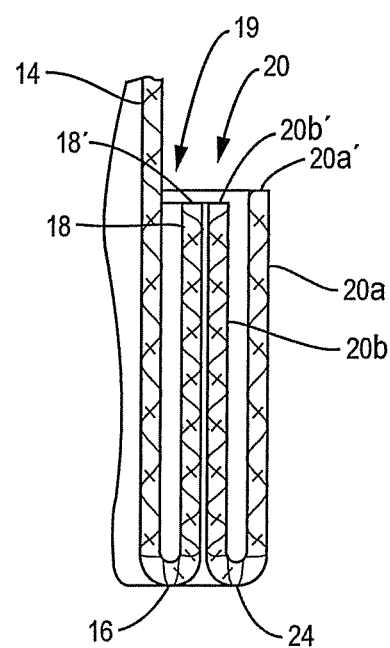
FIG. 4 is a sectional view on a larger scale taken along line 4-4 of FIG. 2.

In any event, a panel 20 encircles rim 19. While that panel may be constituted by a single layer or ply, the illustrated panel is composed of flexible material folded back on itself along a fold line 24 at the bottom of the hat to provide a panel 20 composed of at least two layers, including an outer layer 20a having an upper edge 20a' and an inner layer 20b having an upper edge 20b'. As best seen in FIG. 4, preferably the outer layer 20a extends up higher then all the other layers of the panel and higher then the rim ply 18 so that it conceals the upper edges of those inner layers or plies.

Figure 3:
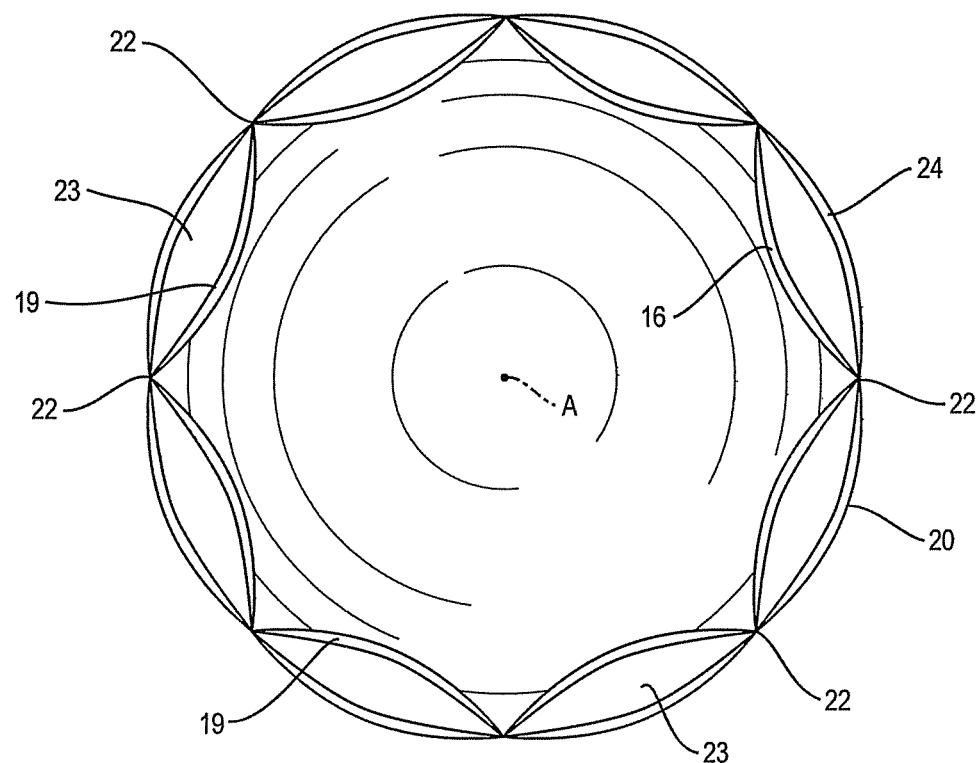
FIG. 3 is a bottom view of the FIG. 2 hat.

As shown in FIGS. 2 and 3, the panel 20 is selectively secured to rim 19. While securements such as staples, buttons, etc. are possible, preferably the securements are lines of stitching 22 spaced apart around the entire perimeter of the panel. Each stitching line 22 extends substantially parallel to axis A the full height of the panel so as to provide a plurality, herein eight, relatively long channels 23 also extending parallel to axis A. Desirably, as best seen in FIG. 3, the lines of stitching penetrate and secure together all of the layers of panel 20 as well as all of the plies of rim 19 so that the panel 20 cannot pull away from the hat walls 14 at the stitching lines 22. Resultantly, the channels retain their parallel orientation with respect to the hat axis A.

Returning to FIG. 1, the ventilator patient interface 11 comprises a CPAP nasal cannula 32 with two flexible tubular prongs 32a designed to extend into the neonate's nares. Cannula 32 has an inspiratory elbow 34a at one end and an expiratory elbow 34b at its opposite end. An inlet tube 36a leading from an oxygen source (not shown) as connected to elbow 34a while an outlet tube 36b extends from the expiratory elbow 34b to an isolated exhaust line (not shown). Preferably, tubes 36a and 36b are corrugated as shown to enhance their flexibility.

The illustrated patient interface 11 is more or less standard and differs from the prior art in that it is stabilized by the hat 10. More particularly and as shown in FIG. 1, the interface 11 is positioned with the tubes 36a and 36b extending through selected ones of the channels 23 of hat 10 and with the prongs 32a of cannula 32 projecting into the nasal passages of neonate N. Preferably, the tubes are adjusted along their respective channels so that the cannula 32 lays more or less horizontally on the neonate's face, i.e. perpendicular to axis A. Once positioned thusly, the walls of the channels 23 resiliently engage the tubes 36a, 36b sufficiently to maintain them in that position wherein they extend more or less parallel to the A of hat 10. It helps in this respect that the walls of the channels 23 tend to conform to the tubing corrugations to enhance the frictional engagement of the hat to the tubing. Accordingly, the tubes 36a, 36b tend to remain fixed relative to hat 10 thereby stabilizing cannula 32 even though the neonate N may shift position or be repositioned by a caregiver.

It is apparent from the foregoing that the hat 10, being flexible and stretchable, may be worn by infants having various head sizes. Also, since the hat has channels 23 all around the axis A of the hat, the tubes 36a, 36b may be placed at the most convenient locations around the hat and be spaced apart appropriately.

Thus, by wearing hat 10, an infant is less likely to be deprived of oxygen due to prongs 32a being pulled from the infant's nose or be discomforted because of unwanted repositioning of cannula 32 with respect to the infant's head.

It is apparent from the foregoing that hat 10 is easy to make and should cost not much more than the price of a conventional infant's hat. Furthermore, the hat is easy to use and when in use is much more aesthetically pleasing to the eye than the prior stabilizing devices described at the outset.

It will thus be seen that the objects set forth above, among those made apparent from the preceding description, are efficiently attained. Also, certain changes may be made in the above construction without departing from the scope of the invention. For example, the hat 10 can also be used to stabilize a single tube ventilator or some other tube leading to or from a patient's nose or mouth. Therefore, it is intended that all matter contained in the above description as shown on the accompanying drawings shall be interpreted as illustrative and not in a limiting sense.

It is also to be understood that the following claims are intended to cover all of the generic and specific features of the invention described herein.

The invention claimed is:

1. A ventilation apparatus comprising a hat having an axis of symmetry and composed of a top and sides leading down to a rim extending all around the hat, an elongated flexible panel encircling the rim, an upper portion of the hat which is not encircled by the elongated flexible panel, and securements securing said elongated flexible panel to the rim at spaced-apart locations therearound to provide a plurality of adjoined channels between the rim and the elongated flexible panel, said plurality of adjoined channels extending parallel to said axis of symmetry and being sized to slidably receive tubing.

2. The ventilation apparatus defined in claim 1 wherein the hat and/or the elongated flexible panel are of a knitted or woven material.

3. The ventilation apparatus defined in claim 1 wherein the securements are lines of stitching extending parallel to said axis of symmetry.

4. The ventilation apparatus defined in claim 1 wherein the elongated flexible panel has at least two layers.

5. The ventilation apparatus defined in claim 1 wherein said sides of the hat are folded back on themselves to provide a two-ply rim, and the securements secure said elongated flexible panel to the two-ply rim.

6. The ventilation apparatus defined in claim 5 wherein the elongated flexible panel is folded back on itself to form at least two layers, and the securements are lines of stitching extending parallel to said axis of symmetry and penetrating all of the at least two layers and the two-ply rim.

7. The ventilation apparatus defined in claim 6 wherein the at least two layers have an outer layer and at least one inner layer, the outer layer extending higher than the two-ply rim and the at least one inner layer.

8. The ventilation apparatus defined in claim 1 and further including one or more tubing segments extending through and captured by a corresponding number of different channels so that each of the one or more tubing segments remains substantially parallel to said axis of symmetry.

9. The ventilation apparatus defined in claim 8 wherein a pair of tube segments extend through a pair of spaced-apart channels, said pair of tube segments having ends positioned below said rim, and a patient interface cannula is connected between said ends.

10. A ventilation apparatus comprising a hat having an axis of symmetry and a top and sides leading down to a rim extending all around the hat, an elongated flexible panel attached to the rim, and encircling the rim and upper portion of the hat which is not encircled by the elongated flexible panel, and a plurality of adjoined channels extending parallel to the axis of symmetry between the rim and the elongated flexible panel, the plurality of adjoined channels configured to receive tubing.

11. The ventilation apparatus of claim 10 wherein the hat and/or the elongated flexible panel are of a knitted or woven material.

12. The ventilation apparatus of claim 10 wherein the elongated flexible panel is attached to the rim at spaced-apart locations on the rim by lines of stitching extending parallel to the axis of symmetry.

13. The ventilation apparatus of claim 10 wherein the elongated flexible panel has at least two layers.

14. The ventilation apparatus of claim 10 wherein the sides of the hat are folded back on themselves to provide a two-ply rim, and the elongated flexible panel is attached to the two-ply rim.

15. The ventilation apparatus of claim 10 further comprising one or more tubing segments extending through and captured by a corresponding number of different channels so that each of the one or more tubing segments remains substantially parallel to said axis of symmetry.

16. A ventilation apparatus comprising:
a hat having an axis of symmetry and composed of a top and sides, the sides folded back on themselves to provide a two-ply rim;
an elongated flexible panel encircling the two-ply rim, an upper portion of the sides which is not encircled by the elongated flexible panel; and
securements securing said elongated flexible panel to the two-ply rim at spaced-apart locations therearound to provide a plurality of adjoined channels between the rim and the elongated flexible panel, said plurality of adjoined channels extending parallel to said axis of symmetry and being sized to slidably receive tubing.

17. The ventilation apparatus defined in claim 16 wherein the securements are lines of stitching extending parallel to said axis of symmetry.

18. The ventilation apparatus defined in claim 16 wherein the hat and/or the elongated flexible panel are of a knitted or woven material.

19. The ventilation apparatus defined in claim 16 wherein the elongated flexible panel has at least two layers.

20. The ventilation apparatus of claim 16 further comprising one or more tubing segments extending through and captured by a corresponding number of different channels so that each of the one or more tubing segments remains substantially parallel to said axis of symmetry.

\* \* \* \* \*

UNITED STATES PATENT AND TRADEMARK OFFICE
CERTIFICATE OF CORRECTION

PATENT NO. : 9,072,856 B2  
APPLICATION NO. : 13/204782  
DATED : July 7, 2015  
INVENTOR(S) : Paula Reynolds et al.

Page 1 of 1

It is certified that error appears in the above-identified patent and that said Letters Patent is hereby corrected as shown below:

In the Claims:  
Claim 10, Col. 5, line 4, should read  
attached to the rim and encircling the rim, an upper portion Signed and Sealed this  
Eighth Day of December, 2015

Michelle K. Lee  
*Director of the United States Patent and Trademark Office*